US00PP25841P3

(12) United States Plant Patent
Schoone

(10) Patent No.: US PP25,841 P3
(45) Date of Patent: Aug. 25, 2015

(54) ***PHALAENOPSIS* ORCHID PLANT NAMED 'EVERLY BEAR'**

(50) Latin Name: *Phalaenopsis hybrida*
Varietal Denomination: Everly Bear

(71) Applicant: Floricultura, Heemskerk (NL)

(72) Inventor: René Schoone, Assendelft (NL)

(73) Assignee: Floricultura, Hemskerk (NL)

( * ) Notice: Subject to any disclaimer, the term of this patent is extended or adjusted under 35 U.S.C. 154(b) by 152 days.

(21) Appl. No.: 13/986,292

(22) Filed: Apr. 19, 2013

(65) Prior Publication Data

US 2013/0291249 P1 Oct. 31, 2013

Related U.S. Application Data

(60) Provisional application No. 61/638,450, filed on Apr. 25, 2012.

(30) Foreign Application Priority Data

Apr. 26, 2012 (NL) ..... PBR OPS0916

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Everly Bear' particularly characterized by flowers which are white/green with purple marks; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Everly Bear'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Everly Bear'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Everly Bear' is a product of a controlled breeding program conducted by the inventor, Rene Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Everly Bear' originated from a cross made by the inventor in 1999 in Strengweg, Heemskerk, The Netherlands. The female or seed parent is the *Phalaenopsis* cultivar designated 'Tzeng-Wen Sentra', unpatented. The male or pollen parent is the *Phalaenopsis* cultivar designated 'Cygnus', unpatented. The new *Phalaenopsis* 'Everly Bear' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Everly Bear', which in combination distinguish this *Phalaenopsis* as a new and distinct cultivar:

1. flowers which are green/white with purple marks;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Everly Bear', the female parent 'Tzeng-Wen Sentra' has red/purple colored flowers and the male parent 'Cygnus' has white colored flowers, whereas the flowers of 'Everly Bear' are white/green with purple marks.

Presently, the commercial cultivars to which 'Everly Bear' can be meaningfully compared are 'Moondance' (U.S. Plant patent application Ser. No. 13/986,291) and 'Gold City' (U.S. Plant patent application Ser. No. 13/986,295). The shape of the petals and sepals and the amount of purple marks of the three plants differ. The petals and sepals of 'Gold City' are more ovate/rounder than the petals and sepals of 'Everly Bear' and 'Moondance'. 'Gold City' has the least purple marks. Mainly around the center. 'Everly Bear' has beyond that also a striking large mark on its dorsal sepal. 'Moondance' has even more marks on the petals and sepals than 'Everly Bear'.

BRIEF DESCRIPTION OF THE PHOTOGRAPHS

The accompanying photographs illustrate the overall appearance of the new *Phalaenopsis* 'Everly Bear' showing the colors as true as is reasonably possible with colored reproductions of this type. Colors in the photographs may differ slightly from the color values cited in the detailed botanical description, which accurately describe the color of 'Everly Bear'.

DETAILED BOTANICAL DESCRIPTION

Figure 1:
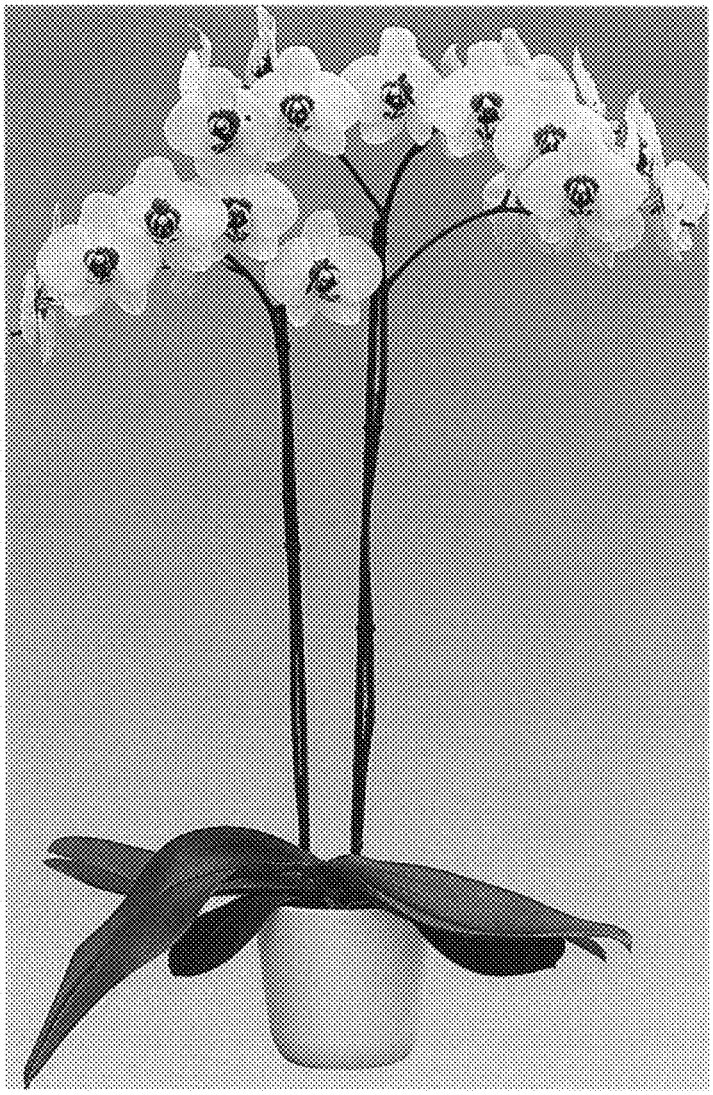
FIG. 1 shows a side view perspective of a typical flowering plant of 'Everly Bear' in a 12 cm pot, at 16 months of age.

The new *Phalaenopsis* cultivar 'Everly Bear' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Everly Bear' as grown in a greenhouse in Strengweg, Heemskerk, The Netherlands, under conditions which closely approximate those generally used in commercial practice. Initially, the ideal temperature to grow plants of 'Everly Bear' is 27° C. during the day and at night. Then, during the flowering phase of 'Everly Bear', the ideal growing temperature is 20-22° C. during the day and 18° C. at night. Light levels for growing 'Everly Bear' are a minimum of 5,000 lux and a maximum of 10,000 lux. A balanced fertilizer with level of 200 ppm N, 87 ppm P, 168 ppm K is applied. Duration of growth of 'Everly Bear' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Everly Bear' plants described is 12 months after potting.

Classification:

*Botanical.*—*Phalaenopsis hybrida.*

Parentage:

*Female or seed parent.*—*Phalaenopsis* cultivar designated 'Tzeng-Wen Sentra', unpatented.

*Male or pollen parent.*—*Phalaenopsis* cultivar designated 'Cygnus', unpatented.

Propagation:

*Type.*—Tissue culture.

*Rooting habit and description.*—Fleshy; approximately 3 mm-7 mm wide and green in color (RHS 191B); freely branching. It takes 12 weeks for plants growing in tissue culture to initiate roots.

Plant:

*Size at maturity.*—Height (from bottom of pot to highest flower): about 60 cm to 70 cm. Spread: about 65 cm.

*Growth habit.*—Standard; green leaves (RHS N137A) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 5 to 6 leaves are produced before flowering.

*Arrangement and attachment.*—Half up/horizontal and on two sides.

*Overall shape of leaf.*—Oval, the tip is blunt and asymmetric.

*Texture* (*upper & underside*).—Smooth and leathery.

*Pubescence.*—None.

*Mature leaf length.*—About 15 to 29 cm.

*Mature leaf width.*—About 6 to 10 cm.

*Mature leaf thickness.*—About 2 mm.

*Mature leaf color.*—Upper side: green (RHS N137A). Under side: green (RHS 138A) with edges RHS N137C.

*Leaf base.*—Acute.

*Margin.*—Entire.

*Venation.*—*Pattern: parallel. Color of midvein: upper side: green (RHS N*137A). Under side: red/purple (RHS 138A).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 7 to 12. Length: about 60 to 70 cm.

*Peduncle.*—Diameter: about 4 to 6 mm. Strength: strong. Aspect: upright. Texture: glabrous and smooth. Color: grey/brown (RHS N199A) with yellow/green spots (RHS 144B).

*Buds.*—Height (from base to tip): about 33 mm. Diameter (at midpoint): about 26 mm. Shape: egg-shaped. Color: green (RHS 143C).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
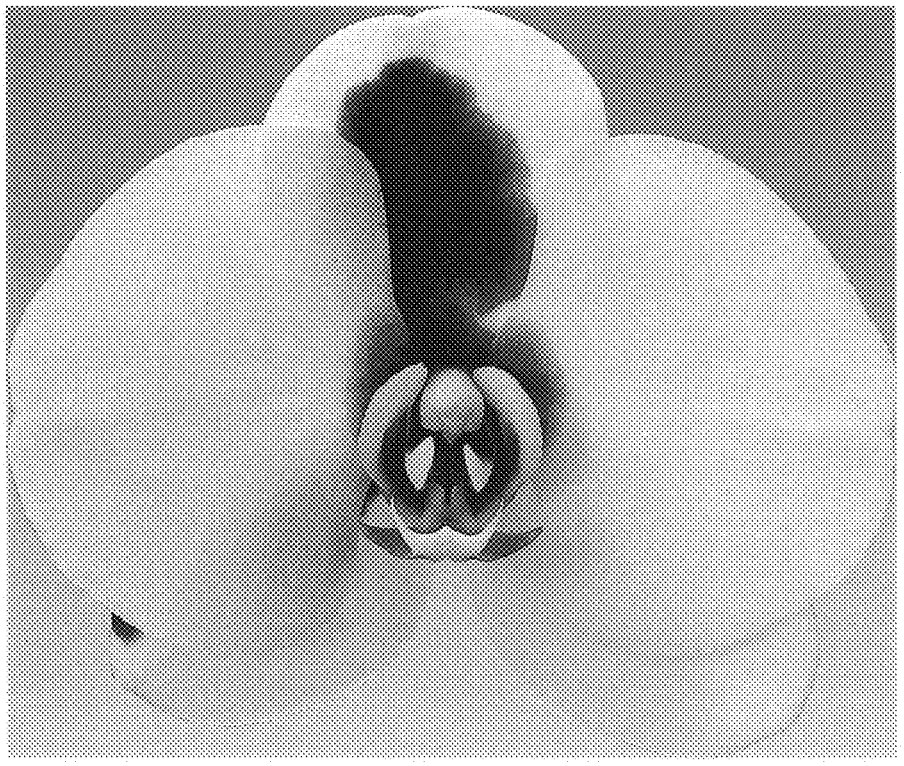
FIG. 2 shows a close-up view of a typical flower of 'Everly Bear'.
Figure 3:
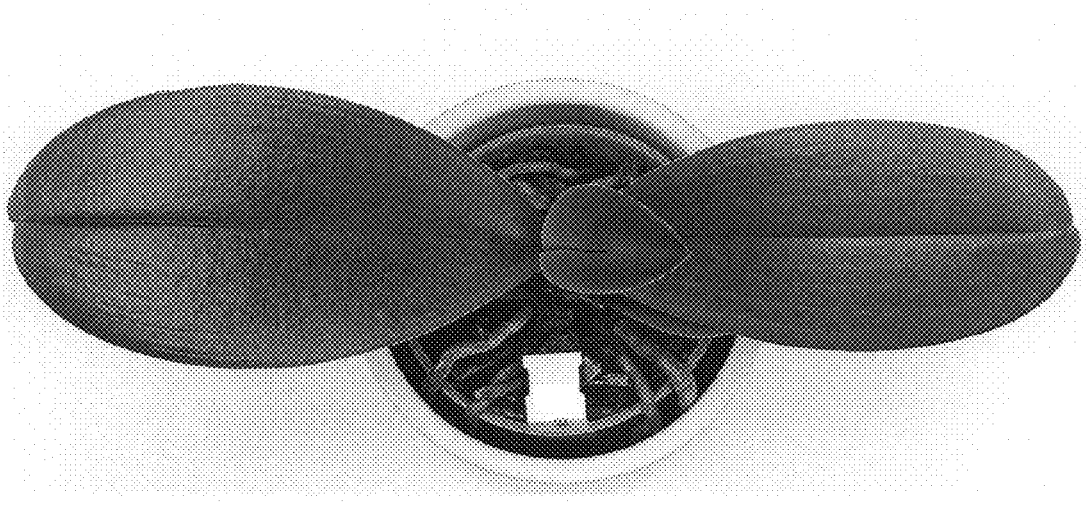
FIG. 3 shows a close-up view of the typical leaves of 'Everly Bear'.

*Flower.*—Rate of opening: Flowers fully opened about 2 to 3 days after petal and sepal separation. Orientation at opening: slanted upward and outward. Shape: typical shape of *Phalaenopsis* orchid; see FIG. 2. Size (of single bloom): Height: about 85 mm to 90 mm. Diameter: about 85 mm to 92 mm. Quantity and arrangement: three petals and three sepals that are trimerous, overlapping and arranged in 2 whorls. Petals are more pronounced than sepals.

*Petals.*—Arrangement: Inner whorl comprises 3 petals: 2 lateral petals and a labellum. 2 lateral petals: Overall shape: broadly ovate and weakly cupped. Apex: oval. Margin: entire and weakly undulate. Base: broadly ovate. Length: about 55 mm. Width: about 40 mm. Texture: Upper surface: smooth and satiny. Under surface: smooth and satiny. Color (when fully opened): upper side: main color is white (RHS 155C); at the base purple (RHS N79B) with purple edges (RHS 77B). Under side: main color is white (a combination between RHS 155C and RHS 157B); at the base some purple (RHS 79C) and some purple/violet (RHS N80A). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Apex: lateral lobes: oval. Midlobe: round corners. Length: about 20 mm. Width (not flattened): about 18 mm. Depth of tube created by lateral lobes: about 11 mm. Texture: Upper and under surface: smooth and satiny. Color (when fully opened): Midlobe: upper surface: at the base little white (RHS NN155C). From base to corners a yellow/orange border (RHS 14A) which runs into a haze of red/purple (RHS 58A). In the center a grey/orange line (RHS 177A). On the edges also RHS 177A. From halfway purple (RHS N81A which runs into RHS N80A. At the end some white (RHS NN155C). Under surface: from chirri white (RHS NN155D). At the edges and in the center red/purple (RHS N81A), after that on the edges RHS 177A. From the corners some yellow/orange (RHS 16A) and at the base violet (RHS 83D). Lateral lobes: upper surface: at the base red/purple (RHS N79A with a lighter edge (RHS N80A). The lower edge is yellow/orange (RHS 14B) and the top is white (RHS NN155D). Under side: at the base purple (RHS 76C, in the center purple (RHS N77A) with a purple edge (RHS N80B). The edges are yellow/orange (RHS 17C) and the top is white (RHS NN155C). Cirrhi: middle (about 6 mm). Color: white (RHS NN155C) with yellow tips (RHS 13B). Pestle (Callosities): Length: about 4 mm. Width (not flattened): about 4 mm. Color: front and sides are yellow/orange (RHS 17C); from the top to the back purple (RHS N77C).

*Sepals.*—Arrangement: Outer whorl comprises 3 sepals. Overall shape: elliptical and weakly cupped. Margin: entire and weakly undulate. Length: about 43 mm. Width: about 36 mm. Apex: round/oval. Texture: Upper and under surface: smooth and satiny. Color (when fully opened): upper surface: main color dorsal sepal is white (RHS NN155A) and lateral sepals is green/white (RHS 157B). Both have purple marks (a mixture of RHS N79A and RHS 79A) surrounded by a purple/violet rim (some RHS N80A and some RHS N81B) . Under surface: main color dorsal sepal is white/green (RHS 157C), with a little green (RHS 157A). Some purple spots (RHS N79A) with a purple rim (RHS N81B). Main color lateral sepals is white/green (a mixture of RHS 157A and RHS 145C) with some purple spots (a mixture of RHS N79A and RHS 79A) with a purple rim (RHS N79D).

*Pedicel.*—Length: about 45 mm. Diameter: about 4 mm. Texture: glabrous and smooth. Color: turns from purple (RHS N79B) into green/white (RHS 157A).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 10 mm. Diameter: about 6 mm. Color: white (RHS NN155D) with at the base little purple (some RHS N78D and some RHS N78A).

*Pollinia.*—Quantity: two. Diameter: about 1 mm. Color: yellow/orange (RHS 23A).

*Ovary.*—Length: about 4 mm. Diameter: about 2 mm. Color: white (RHS NN155B) with a little purple (RHS N78D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Everly Bear', as illustrated and described herein.

* * * * *